(12) United States Patent
Cronin (10) Patent No.: US 8,586,897 B2
(45) Date of Patent: Nov. 19, 2013

(54) MICROWAVE APPLICATOR

(75) Inventor: Nigel Cronin, Bath (GB)

(73) Assignee: Angio Dynamics, Inc., Latham, NY (US)

( * ) Notice: Subject to any disclaimer, the term of this patent is extended or adjusted under 35 U.S.C. 154(b) by 710 days.

(21) Appl. No.: 12/206,090

(22) Filed: Sep. 8, 2008

(65) Prior Publication Data

US 2008/0314894 A1 Dec. 25, 2008

Related U.S. Application Data (63) Continuation of application No. 10/530,823, filed as application No. PCT/GB03/04082 on Sep. 15, 2003, now abandoned.

(30) Foreign Application Priority Data

Oct. 10, 2002 (GB) .................... 0223564.6

(51) Int. Cl.
*H05B 6/70* (2006.01)
*A61B 18/04* (2006.01)

(52) U.S. Cl.
USPC ........................................... 219/690; 606/33

(58) Field of Classification Search
USPC ......... 219/690, 693–694, 696, 710, 712, 750, 219/751; 174/21 C, 28, 102 R, 120 R, 113 C, 174/107; 606/33, 34, 38; 607/156, 154, 96, 607/98, 100–103, 105; 333/26
See application file for complete search history.

(56) References Cited

U.S. PATENT DOCUMENTS

| 3,065,752 | A |  | 11/1962 | Potzl |
|---|---|---|---|---|
| 3,461,261 | A |  | 8/1969 | Lewis et al. |
| 4,446,874 | A |  | 5/1984 | Vaguine |
| 4,476,363 | A |  | 10/1984 | Berggren |
| 6,635,055 | B1 | * | 10/2003 | Cronin ........................... 606/33 |
| 2006/0151485 | A1 |  | 7/2006 | Cronin |
| 2008/0314894 | A1 |  | 12/2008 | Cronin |

FOREIGN PATENT DOCUMENTS

| AU | 2003267607 B2 | 5/2004 |
|---|---|---|
| CA | 2 339 277 A1 | 11/1999 |
| EP | 0 294 854 A2 | 12/1988 |
| GB | 2 074 826 A | 11/1981 |
| JP | 2002109971 A * | 4/2002 |

* cited by examiner

*Primary Examiner* — Quang Van
(74) *Attorney, Agent, or Firm* — Peter J. Flora (57) ABSTRACT

A microwave applicator has a coaxial electrical input (4) and a waveguide (1) filled with dielectric (2), an inner conductor (7) of the coaxial input extending longitudinally within one end of the waveguide to launch microwaves in the TM01 mode to travel to the distal end face (8) of the waveguide so that microwaves are transmitted when the distal end face is contacted by the biological tissue to be treated.

3 Claims, 7 Drawing Sheets

MICROWAVE APPLICATOR

TECHNICAL FIELD

This application is a continuation of prior application Ser. No. 10/530,823, filed Nov. 18, 2005, now abandoned and claims the benefit of International Application No. PCT/GB2003/004082, filed on Sep. 15, 2003, and claims the benefit of GB Application No. 0223564.6, filed Oct. 10, 2002. This invention relates to a microwave applicator suitable for heating biological tissue and a method of heat treating surface tissue.

The applicants have previously proposed a microwave applicator for surgical use comprising a waveguide of reduced diameter by virtue of containing a dielectric of high permittivity. A coaxial electrical input generates microwaves in the $TE_{11}$ mode within the dielectric and these radiate from the distal end face of the waveguide.

DISCLOSURE OF THE INVENTION

According to a first aspect, the present invention, consists in a microwave applicator comprising a coaxial electrical input and a waveguide filled with dielectric, a central conductor of the coaxial input extending longitudinally within one end of the waveguide to launch microwaves preferably in the $TM_{01}$ mode, to travel to the distal end face of the waveguide so that microwaves are transmitted from the distal end face when in contact with the biological tissue to be treated.

The $TM_{01}$ mode is preferred because it has a field pattern that is a good match with the coaxial input, better than the fundamental $TE_{11}$ mode more commonly used. The $TM_{01}$ also produces a simple transition between the coaxial input and the waveguide. The central conductor is preferably coaxially aligned within a circular waveguide and extends a short way within the waveguide to match the general dimensions of the waveguide, especially its length and diameter, and the permittivity of the dielectric and frequency of the electrical input.

The distal end face of the waveguide is preferably flat and radiates microwave energy with parallel wavefronts that advance into the biological tissue in contact with the distal end face and have minimum lateral spreading. The depth of penetration of the microwaves is dependent upon the frequency and electrical input power, but typically only a small distance of penetration is required for local heat treatment of tissue in microsurgery. In an alternative embodiment, the distal end face may be slightly domed and centred on the axis of the waveguide instead of being flat.

Another particularly important feature of the invention is the ability to make use of resonance in the waveguide so that reflections from the transition at the input end, and from the distal end face caused by the change in dielectric at each, are out of phase and therefore enhance forwards transmission when the distal end face is in contact with the biological tissue, and are in phase and therefore enhance reflection to the coaxial input when the distal end face is out of contact with the biological tissue. Therefore, microwave energy is only transmitted to any appreciable extent from the distal end face when in contact with the biological tissue to be treated, and this is a key safety feature in the mode of operation.

According to a second aspect, the invention consists in a microwave applicator comprising a waveguide, a coaxial electrical input with a central conductor extending longitudinally within one end of the waveguide to launch microwaves preferably in the $TM_{01}$ mode, that travel to the distal end of the waveguide and are transmitted into biological tissue to be treated, a diaphragm of low loss dielectric material being provided within the waveguide so as to extend laterally of the waveguide to reflect the microwaves travelling along it, the longitudinal location of the diaphragm being selected in relation to the ends of the waveguide so that the coherent addition of the reflected waves from the waveguide junction and the diaphragm combine to create a wave which is of correct magnitude and phase to cancel the reflection from the coaxial waveguide junction.

Preferably, the thickness of the diaphragm and the permittivity of the dielectric material from which the diaphragm is made are selected to determine the magnitude of the rearward reflection of microwaves from the diaphragm for optimum cancellation of the rearward reflection in the coaxial input.

Preferably, the waveguide is air-filled, and the distal end of the waveguide is adapted to contact (or nearly contact) the surface tissue to be treated.

The microwave applicator of the first or second aspect of the invention can be used in a method of heat treating surface tissue, the distal end face of the waveguide being brought into contact with the surface tissue for treatment.

DESCRIPTION OF THE DRAWINGS

The invention will now be described by way of example with reference to the accompanying drawings, in which.

EMBODIMENTS OF THE INVENTION

Figure 1:
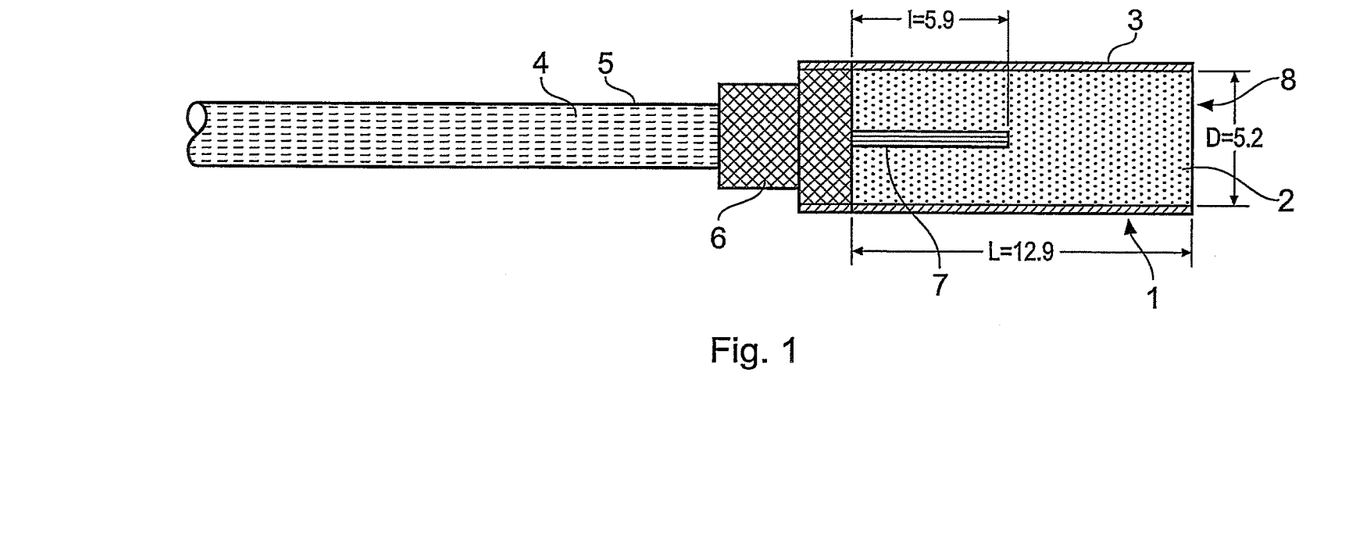
FIG. 1 is an axial section of a flexible laparoscopic microwave applicator according to a first embodiment of the invention.

The microwave applicator of FIG. 1 consists of a waveguide 1 formed by a cylindrical body of dielectric 2 covered in an outer layer of aluminium foil 3, and a flexible coaxial cable input power supply 4 which is connected to the waveguide at one end so that the outer conductor 5 of the coaxial cable is electrically connected via a copper ferrule 6 to the aluminium tape 3, and the inner conductor 7 of the coaxial cable extends axially a short distance l into the dielectric body 2. The distal end face 8 of the waveguide 1 is flat and is covered by a layer of a non-stick polymer coating such as FEP or paralene.

The waveguide 1 preferably operates in the $TM_{01}$ mode.

Typically, for this microwave applicator to operate at a frequency of 9.2 GHz the dimensions of the waveguide are as follows; overall length L=12.9 mm, diameter D=5.2 mm, l=5.9 mm; and the permittivity of the dielectric body k=25. The dielectric is typically, Hik 500f dielectric material sold by Emerson & Cummings.

Figure 2:
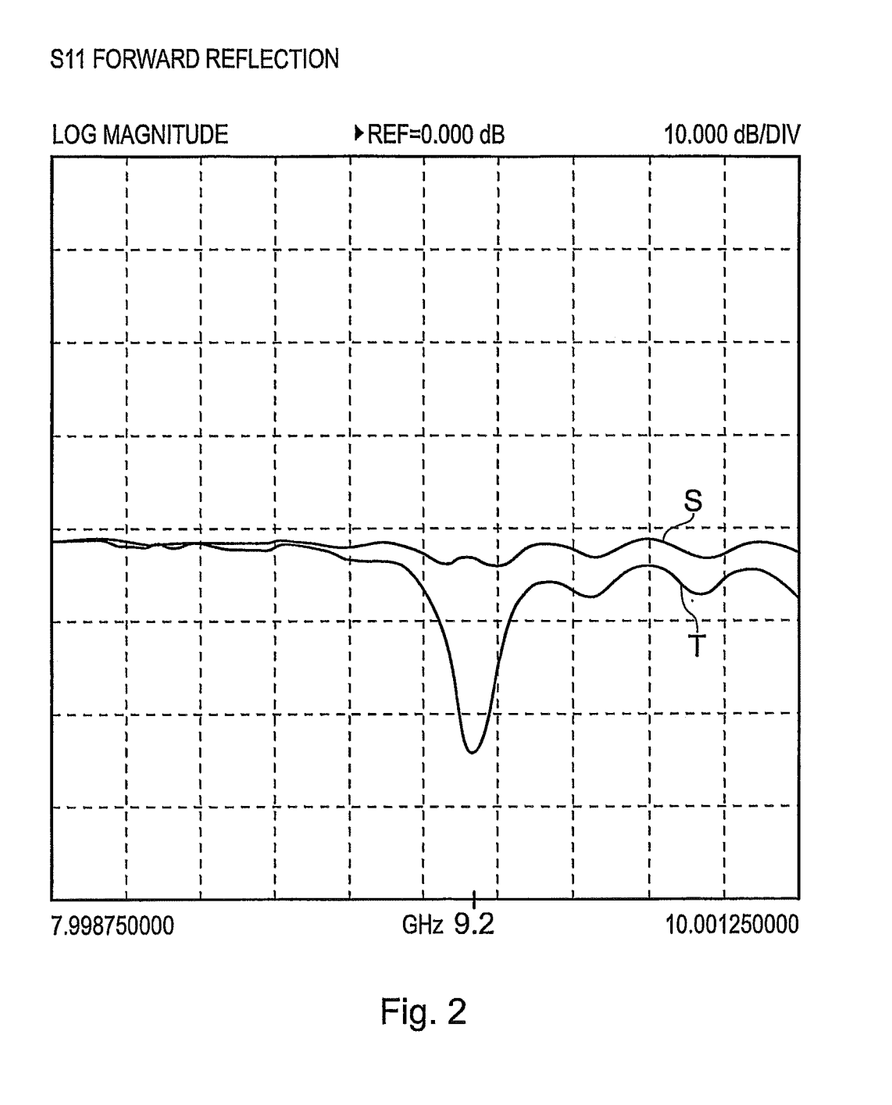
FIG. 2 shows graphs of reflection coefficient against microwave frequency for the applicator of FIG. 1 when the distal end is in air (graph S) and when in contact with biological tissue (graph T)

The performance of the microwave applicator of FIG. 1 at different frequencies is shown by the graphs of FIG. 2, in which Graph S shows the variation of reflection coefficient $S_{11}$ when the distal end face 8 of the applicator is in air, and in which Graph T shows the variation of reflection coefficient $S_{11}$ when the distal end face 8 of the applicator is in contact with biological tissue to be treated. A drop in value of $S_{11}$ in FIG. 2 is indicative of a good microwave match, which is clearly demonstrated in Graph T at the designed operating frequency of 9.2 GHz. Under these conditions, the applicator is transmitting maximum microwave energy into the biological tissue, but if the contact with the tissue is broken and the distal end face is in air or gas such as $CO_2$, then the transmitted energy falls immediately to a much lower level as the energy is reflected back to the coaxial cable input power supply 4.

It will be appreciated that a microwave applicator as shown in FIG. 1 can be relatively inexpensive to manufacture, and can therefore be sold as a disposable product for microsurgery.

The microwave applicator of FIG. 1, being of reduced diameter of 5.2 mm, is suitable for insertion through a Trocar in laproscopic surgery to produce a local heating effect in a controlled manner adjacent the distal end face when in contact with biological material. For example, such an applicator may be used to destroy small surface tumours, for the treatment of ovarian cancer, or the treatment of endometriosis, or any surface lesions.

Figure 3:
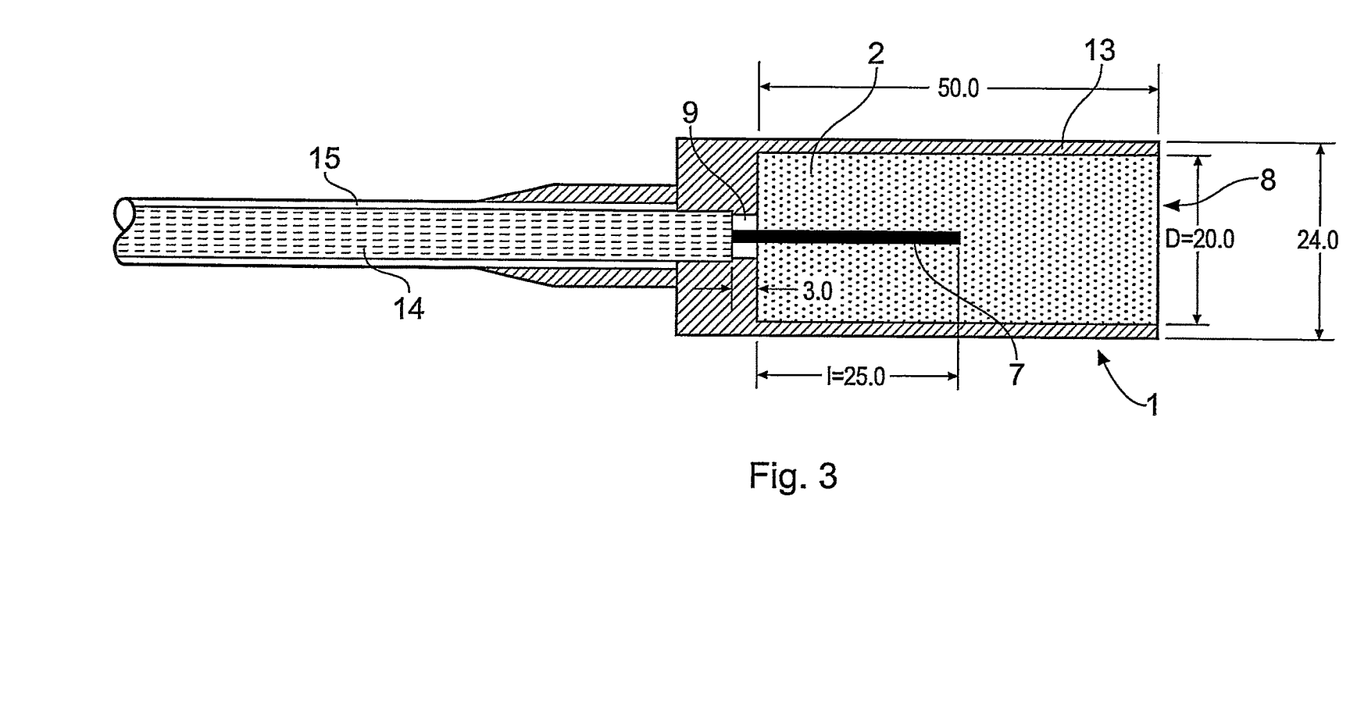
FIG. 3 is an axial section of a microwave applicator according to a second embodiment of the invention.

The second embodiment of the invention shown in FIG. 3 is similar in configuration to that of FIG. 1, and the same reference numbers are used for equivalent components. However, the waveguide 1 comprises a rigid aluminium cylindrical wall 13, typically 2 mm thick, and the dielectric body 2 is composed of a hard ceramic material, such as stabilised zirconia (TECHNOX® 2000) which has a permittivity K=25. This dielectric material gives the applicator an ability to handle higher power levels, typically, up to 200 watts, compared with a power level of, say, 45 watts for the applicator of FIG. 1. The waveguide 1 preferably operates in the $TM_{01}$ mode.

The applicator of FIG. 3 is designed to operate at a lower frequency of 2.45 GHz, and also has an increased length L=50 mm and diameter D=20 mm. It will be appreciated that the diameter D is determined by the frequency of operation and permittivity K, and is selected to allow treatment of an appropriate size area of tissue, the increased area compared with FIG. 1 being balanced by the increased power to provide an appropriate power density at the distal end 8 for the treatment intended.

The projection l of the central conductor 7 extends 25 mm into the dielectric body 2, and an air gap 9 is provided between the outer conductor 5 and dielectric of the coaxial cable input 4 and the waveguide 1 to allow the dielectric filling of the coaxial cable to expand.

The applicator of FIG. 3 with a larger distal end 8 is more suitable for the treatment of larger surface breaking tumours, for example, primary and secondary tumours on the liver.

In an alternative embodiment of the invention, suitable for treating smaller liver tumours, the same configuration as that of FIG. 3 is used but, the stabilised zirconia dielectric is replaced by alumina having a permittivity K=10, and the dimensions are as follows: L=18 mm; D=10 mm; l=11 mm; and the operating frequency is 9.2 GHz. This applicator will treat a small area of tissue than that of FIG. 3, but will cause less collateral damage.

Figure 4:
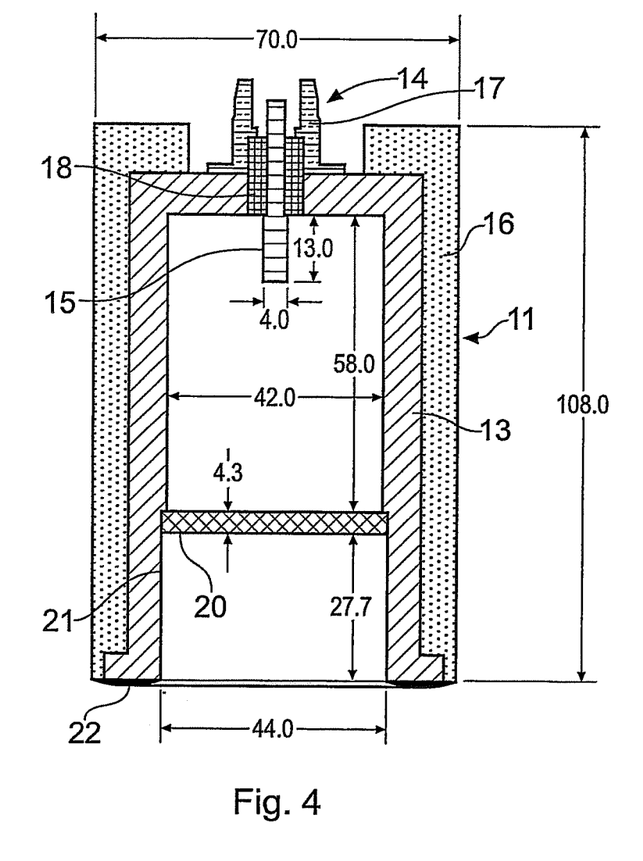
FIG. 4 is an axial section of a microwave applicator according to a third embodiment of the invention.

The microwave applicator shown in FIG. 4 consists of an air-filled waveguide 11 formed by an aluminium cylindrical wall 13 with an input connection 14 for a flexible coaxial cable input power supply which is connected to the waveguide at one end. The outer surface of the wall 13 is covered by a UPVC sleeve 16. The outer conductor of the coaxial cable is electrically connected to the wall 13 of the waveguide via a brass fitting 17, and the inner conductor of the coaxial cable is connected to a conductor 15 which extends axially a short distance l into the waveguide 11. A PTFE bush 18 separates and forms an electrical insulator between the conductor 15 and fitting 17. A Perspex diaphragm 20 is located laterally within the waveguide near the open end within a rebated section 21 which spaces it a distance w away from the open end 18. The diaphragm 20 has a thickness t. The waveguide 11 preferably operates in the $TM_{01}$ mode.

The operating frequency of the applicator is 7 GHz and the dimensions are typically L=108 mm; D=42 mm; l=13 mm; w=27.7 mm; and t=4.3 mm. These dimensions are selected in connection with the operating frequency and permittivity of the diaphragm so that when in use with the open end of the waveguide in contact with surface tissue to be treated, the rearward reflections of microwaves from the tissue and the transition between the coaxial cable 14 and waveguide 11 are substantially cancelled out by the reflections from the diaphragm which reduces reflections within the coaxial cable. In this balance situation, the majority of the microwave energy is then transmitted to the tissue being treated. In particular, the thickness t of the diaphragm 20 and the permittivity k of the material of which it is composed will determine the size of rearward reflection of microwaves from it. The location of the diaphragm 20 relative to the ends of the waveguide 11 will determine the relative phases of the rearward reflections of the microwaves.

A microwave applicator such as that of FIG. 4 would be suitable for skin treatments such as the treatment of psoriasis, especially because the end of the probe has minimal contact with the tissue being treated. Preferably, the edge of the waveguide 11 at the open end may be coated or fitted with some other protection (22) such as silicone rubber, for engagement with the tissue.

Figure 5:
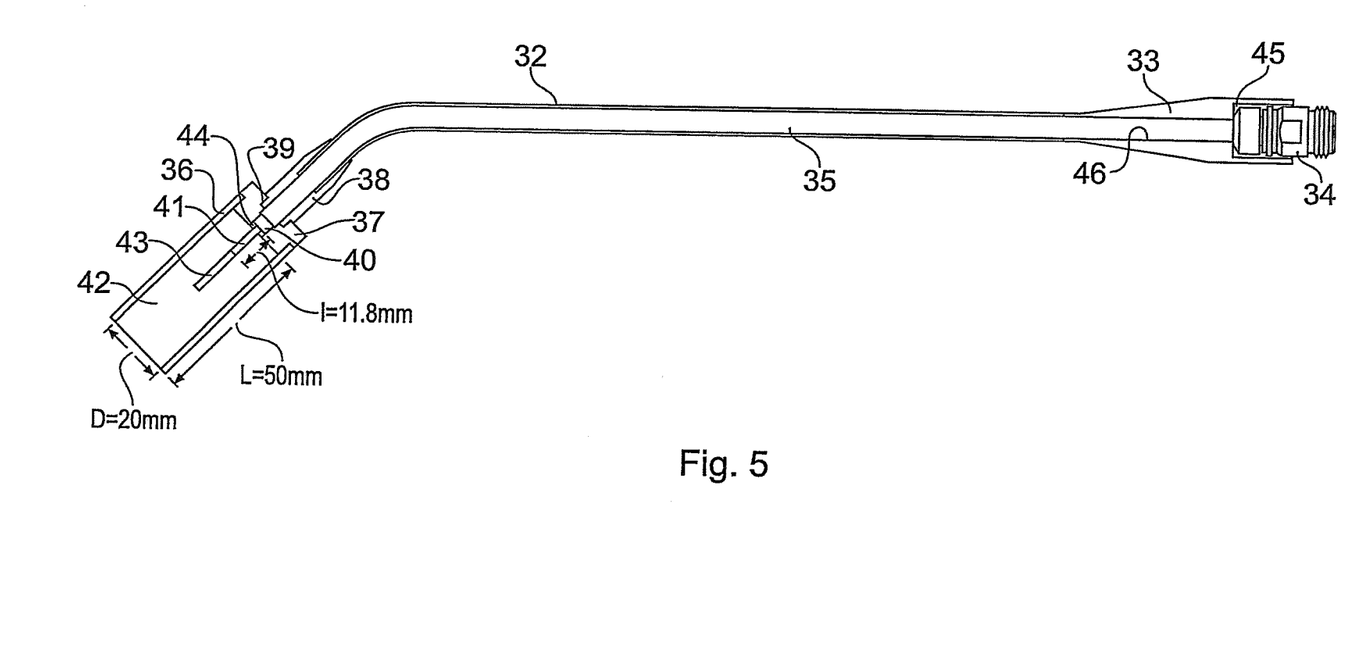
FIG. 5 is an axial section of a microwave applicator according to a fourth embodiment of the invention.

An alternative embodiment of the invention is illustrated in FIG. 5 in which the microwave applicator consists of a waveguide 31 supported at one end of a rigid tube 32 having a handle 33 and input power connection 34 at its other end. The applicator is held and manipulated by the handle 33 and the waveguide 31 forms a treatment head. A coaxial cable 35 extends through the tube 32 and connects the input power connection 34 to the waveguide 31.

The waveguide 31 consists of a cylindrical aluminium sleeve 36 which is connected to an aluminium end cap 37 at the input end. An aluminium support bush 38 is connected at one end to a central bore 39 in the end cap 37, and is connected at its other end to the tube 32 so that the coaxial cable 35 can pass through it. The outer conductor 40 of the coaxial cable 35 is exposed and electrically connected to the end cap 37, and the inner conductor 41 of the coaxial cable 35 is exposed to project axially into the waveguide 31. A cylindrical body 42 of dielectric comprising TECHNOX® 2000 ceramic is fitted within the sleeve 36 and is formed with a central bore 43 to receive the inner conductor 41. An air gap 44 is formed between the end of the dielectric filling 45 of the coaxial cable and the dielectric body 42 of the waveguide.

The handle 33 is machined from aluminium and has a concentric recess 45 at its input end to receive the input power connection 34. A central bore 46 in the handle accommodates the coaxial cable 35.

The waveguide 31 preferably operates in the $TM_{01}$ mode.

Typically, the applicator is designed to operate at 2.45 GHz and the dimensions of the waveguide comprise a sleeve 36 of length L=50 mm and inner diameter D=20 mm, and an inner conductor 41 with an exposed length l=11.8 mm and an air gap 44 of length 2 mm. The tube 32 is typically stainless steel and has a diameter of 8 mm and length 250 mm or other appropriate length to reach tissue being treated. The tube 32 may be bent laterally at one or more locations 46 along its length to improve the ease with which the radiation emitting end face 47 of the treatment head can be engaged in surface-to-surface contact with tissue to be treated.

Figure 6:
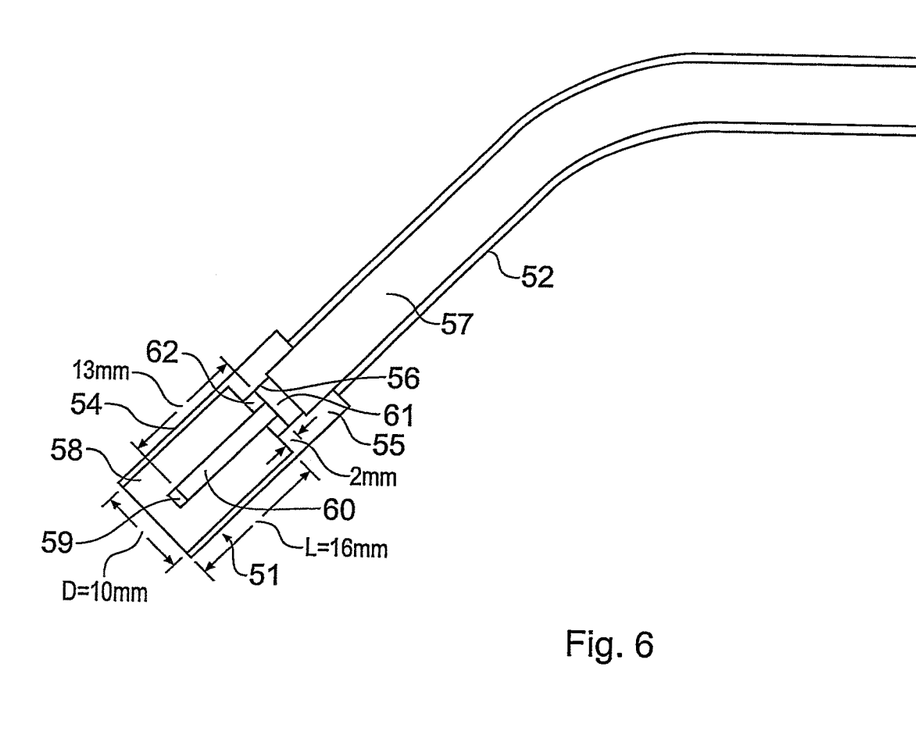
FIG. 6 is an axial section of a microwave applicator according to a fifth embodiment of the invention.

Another embodiment of the invention is illustrated in FIG. 6, which like that of FIG. 5, consists of a waveguide 51 forming a treatment head at one end of a rigid tube 52, and a handle and input power connection (not shown) at the other end of the tube 52. The waveguide 51 consists of a machined aluminium component consisting of a cylindrical sleeve 54 and end wall 55 having an aperture 56 to receive the tube 52 and coaxial cable 57. A cylindrical body of dielectric 58 comprising Hik500f is fitted inside the sleeve 54 and is formed with a central bore 59 to receive the inner conductor 60 of the coaxial cable 57. The outer conductor 61 of the cable 57 is electrically connected to the end wall 55 and an air gap 62 is formed between the end of the dielectric filling 63 of the cable 57 and the dielectric body 58.

Typically, the applicator is designed to operate at 9.2 GHz and the waveguide dimensions comprise a sleeve 54 of length L=16 mm and inner diameter 10 mm, and an inner conductor 60 with an exposed length of 13 mm, and an air gap 62 of 2 mm.

The microwave applicator of FIGS. 5 and 6 can be used, like the applicators of FIGS. 1 and 3, to treat tumours or other surface lesions, or for the treatment of endometriosis. The treatment head is inserted through an opening in a patient's body, either through a Trocar or directly through a larger incision. The applicator is then manipulated to bring the end face of the treatment head into face-to-face contact with the tissue to be treated adjacent the tumour or lesion. Microwave radiation emitted from the end face of the treatment head is then transmitted into the tumour or lesion and surrounding tissue and causes it to be ablated. This process can be repeated as necessary to ablate multiple tumours or lesions at different locations before the treatment is completed.

A microwave applicator according to the invention can also be used to stop the flow of blood from bleeding tissue by bringing the end face of the treatment head into contact with the bleeding tissue and transmitting radiation to ablate the tissue.

Although the methods of medical treatment described above use the microwave applicators illustrated it should be appreciated that the invention also relates generally to the method of treating tumours or lesions on or within the surface of tissue, especially the liver, using any form of microwave applicator having a treatment head with a radiation emitting surface which can engage the tissue in face-to-face contact so as to transmit radiation into the tissue.

Figure 7:
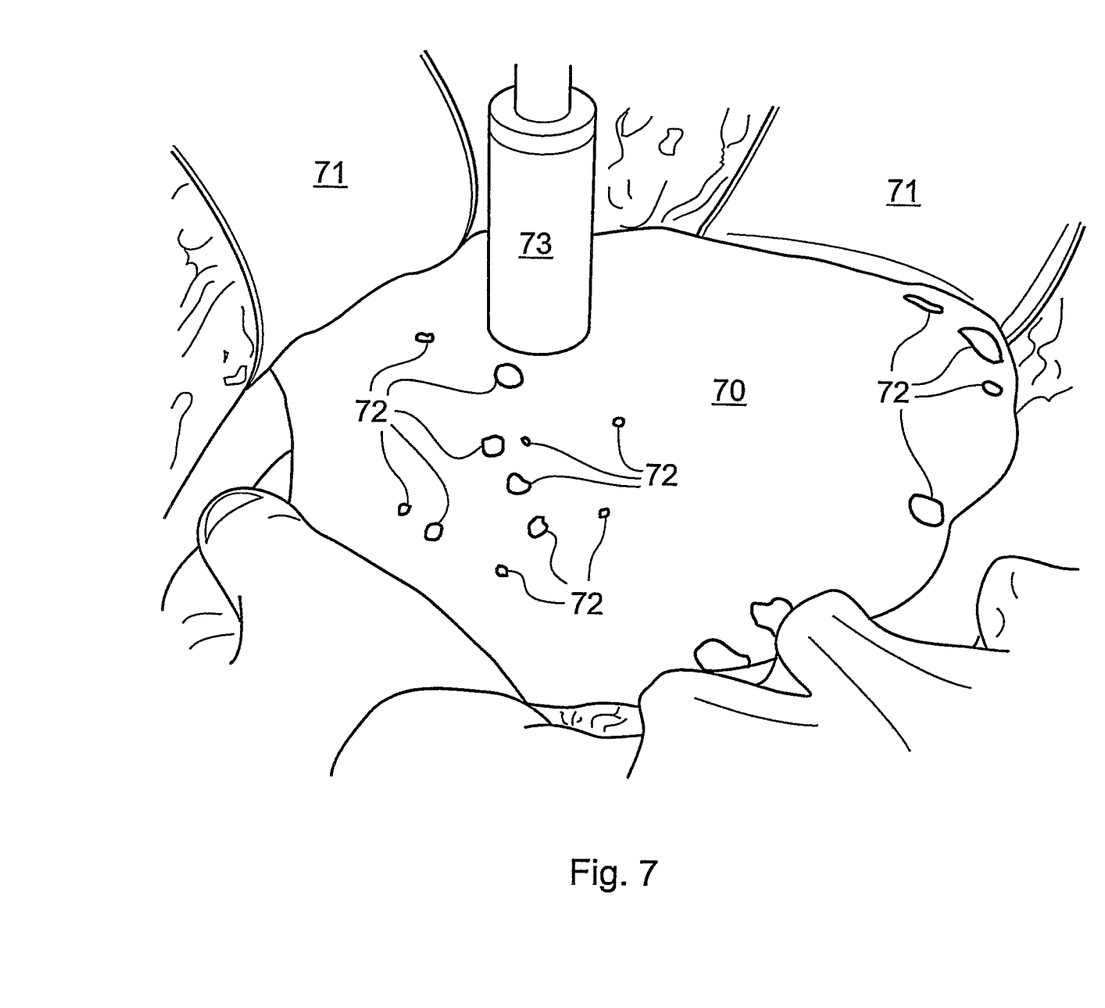
FIG. 7 is a schematic drawing of a microwave applicator in use for medical treatment according to the invention.

FIG. 7 illustrates medical treatment of surface tumours on a patient's liver 70. An incision is made across the patient's abdomen and the abdominal wall is held in clamps 71 to create an opening into the abdominal cavity. The liver is then freed from the surrounding tissue so that it can be accessed for treatment. The condition of the liver is assessed and decisions are made as to the treatment to be given, whether to remove part of the liver and/or to ablate part of the liver. In the drawing, the liver shown has multiple surface tumours 72 which require ablation. A microwave applicator 73, preferably such as illustrated in any of FIGS. 1 to 6, is manipulated to align the end face of the treatment head with a tumour, and to bring the end face into contact with the tumour. The power supply to the applicator is then switched on so that it generates microwaves that irradiate the tumour, causing it to be ablated. The applicator is then lifted away from the liver surface either before or after the power has been reduced or switched-off. The whole process is then repeated multiple times to ablate each of the surface tumours in turn.

Real time intra-operative ultrasound scanning is used to assess the location and extent of the tumours within or on the surface of the liver. Also, the extent of the ablation achieved when treating an individual tumour is assessed using intra-operative ultrasound scanning. The ablated tissue appears as a "thermal cloud" emanating from the end face of the applicator when viewed in the scan output. The treatment is therefore continued until the "thermal cloud" encompasses the whole of the tumour and a safety margin around it.

A larger tumour or tumours may require removal of part of the liver. This is done by cutting the liver, which causes bleeding. The microwave applicator is then used to stem the bleeding by bringing the end face of the treatment head into contact with the bleeding surface and turning on the power to the applicator to ablate the bleeding surface. This procedure is then repeated over the whole of the bleeding surface.

Once treatment of the liver is completed, the abdomen is washed with saline solution, and the abdominal wall is sutured.

The invention claimed is:

1. A microwave applicator comprising a waveguide having an open distal end; a coaxial electrical input with an inner conductor extending longitudinally within a proximal end of the waveguide to launch microwaves in the $TM_{01}$ mode that travel to the open distal end of the waveguide and are transmitted into biological tissue to be treated; a diaphragm of low loss dielectric material being provided within the waveguide between a distal end of said conductor and said open distal end of the waveguide, the diaphragm extending laterally of the waveguide to reflect the microwaves travelling along it, the longitudinal location of the diaphragm being selected in relation to said ends of the waveguide so that the phase of reflections from the diaphragm and said ends serve to reduce or cancel rearward reflections in the coaxial input.

2. A microwave applicator as claimed in claim 1 in which the thickness of the diaphragm, and the permittivity of the dielectric material from which it is made are selected to determine the magnitude of the rearward reflection of microwaves from the diaphragm for optimum cancellation of the rearward reflection in the coaxial input.

3. A microwave applicator as claimed in claim 1 which is air-filled.

* * * * *